United States Patent [19]

Schenk

[11] Patent Number: 4,609,491

[45] Date of Patent: Sep. 2, 1986

[54] TRI- AND TETRA-SUBSTITUTED CYCLOHEXEN-1-METHYL ACETATES AS ODORANTS

[75] Inventor: Hanspeter Schenk, Zumikon, Switzerland

[73] Assignee: Givaudan Corporation, Clifton, N.J.

[21] Appl. No.: 497,340

[22] Filed: May 23, 1983

[30] Foreign Application Priority Data

Jun. 3, 1982 [CH] Switzerland ............... 3398/82

[51] Int. Cl.[4] ............... A61K 7/46; C07C 67/02
[52] U.S. Cl. ............... 252/522 R; 560/220;
560/259; 568/824; 568/826
[58] Field of Search ............... 560/220, 259; 568/824, 568/826; 252/522 R

[56] References Cited

U.S. PATENT DOCUMENTS

| | | | |
|---|---|---|---|
| 3,562,316 | 2/1971 | Julia | 260/497 |
| 3,923,896 | 12/1975 | Schulte-Elte | 568/824 X |
| 4,018,718 | 4/1977 | Ochsner et al. | 252/522 R |
| 4,091,823 | 5/1978 | Kallianos et al. | 131/17 R |
| 4,190,561 | 2/1980 | Auger et al. | 252/522 R |
| 4,271,324 | 6/1981 | Wilson et al. | 568/824 |
| 4,301,018 | 11/1981 | Sprecker et al. | 568/824 X |
| 4,321,164 | 3/1982 | Sprecker et al. | 252/522 R |

FOREIGN PATENT DOCUMENTS 0069245 6/1975 Japan ............... 252/522 R

OTHER PUBLICATIONS

Favre et al., CA 47:6907i (1952).
Boake, CA 58:1500e (1962).
Guiotto et al., CA 93:90132s (1980).
Dawson et al., J. Med. Chem. 1980, 23(9), pp. 1013-1014 (1980).
Arctander, Steffen, "Perfume and Flavor Chemicals", Montclair, N.J., 1969; 767-8, 940-1.

*Primary Examiner*—Anton H. Sutto
*Attorney, Agent, or Firm*—Robert F. Tavares

[57] ABSTRACT

Novel odorant substances of the formula:

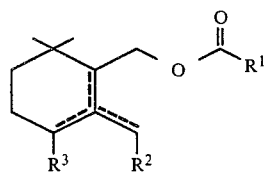

wherein:
one of the three dotted lines represents an optional bond,
$R^1$ represents hydrogen, an alkyl group of one to four carbons or an alkenyl group of two to four carbons,
$R^2$ represents hydrogen or methyl,
$R^3$ represents hydrogen or methyl, provided that $R^2$ and $R^3$ are never both hydrogen, and novel fragrance compositions containing same.

9 Claims, No Drawings

TRI- AND TETRA-SUBSTITUTED CYCLOHEXEN-1-METHYL ACETATES AS ODORANTS

The novel odorant substances provided by the present invention are compounds of the formula:

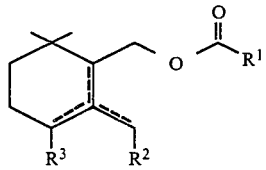
I wherein:
one of the three dotted lines represents an optional bond,
$R^1$ represents hydrogen, an alkyl group of one to four carbons or an alkenyl group of two to four carbons,
$R^2$ represents hydrogen or methyl,
$R^3$ represents hydrogen or methyl provided that,
$R^2$ and $R^3$ are never both hydrogen.

Formula I is intended to embrace all possible stereoisomers especially the geometric isomers of the γ-derivatives in the case of the ring unsaturated compounds and, in the case of the ring-saturated compounds, the stereoisomers which are possible due to the relative configuration of the substituents at the $C_1$-, $C_2$- and $C_3$-atoms.

The alkyl and alkenyl groups denoted by $R^1$ can be straight-chain or branched chain, e.g. methyl, ethyl, propyl, isobutyl, allyl, methallyl etc. Those compounds wherein $R^1$ represents hydrogen, methyl, ethyl, isopropyl or 1-propenyl are preferred with those wherein $R^1$ represents methyl being especially preferred.

The invention is also concerned with a process for the manufacture of the compounds of formula I. This process comprises (a) esterifying an alcohol of the formula:

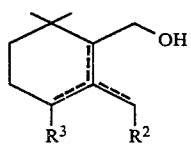
II wherein $R^2$ and $R^3$ and the broken lines have the significance given earlier, or (b) cyclizing an ester of the formula

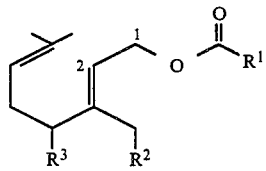
III (which formula is intended to embrace the two double bond stereoisomers in position 2) wherein $R^1$, $R^2$, $R^3$ have the significance given earlier, or (c) catalytically hydrogenating a compound of the formula

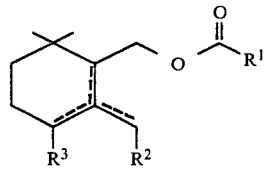
Ia wherein $R^1$, $R^2$ and $R^3$ have the significance given earlier and one of the three broken lines represents an additional bond.

The esterification of the alcohols of formula II can be carried out in a manner known per se using the usual acylating agents (e.g. acyl halides or acid anhydrides). The procedure using acyl halides is preferred. This esterification procedure can be conveniently carried out in the presence of tertiary amines such as pyridine or dimethylaniline.

However, as mentioned above, the esterification can also be carried out using an acid anhydride. The reaction conditions in this case are conveniently the same as those used when the esterification is carried out using an acyl halide.

The esters of formula I can be conveniently purified by distillation under reduced pressure. They are colourless to slightly yellowish coloured liquids. They are insoluble in water, but soluble in organic solvents (e.g. alcohols, ethers, ketones, esters, hydrocarbons and halogenated hydrocarbons).

The cyclization of the esters of formula III can be carried out according to methods known for the manufacture of cyclogeranoyl derivatives; see, for example, Smit et al, Izv. Akad. S.S.S.R. Otd. chin. 1959, 1848.

Suitable cyclizing agents are inorganic and organic protic acids such as sulphuric acid, phosphoric acid, methanesulphonic acid, formic acid, acetic acid etc. Lewis acids such as boron trifluoride, tin tetrachloride, zinc chloride etc.

The cyclization can be carried out in the presence or absence of a solvent. Suitable solvents are inert solvents such as hexane, benzene, nitromethane etc. The temperature is not critical and the cyclization can be carried out at room temperature or at a higher or lower temperature.

The hydrogenation of the double bond(s) present in a compound of formula Ia, usually as a stereoisomer mixture, is carried out catalytically. Suitable catalysts for use in the hydrogenation are noble metal catalysts which contain, for example, platinum, palladium, ruthenium or rhodium.

The hydrogenation can be carried out in the presence or absence of a solvent. Inert solvents such as ethanol, methanol, cyclohexane etc. are preferred.

The hydrogenation can be carried out at temperatures between, for example, 0°–100° C., especially between 15°–30° C., and at normal pressure or at higher pressures such as 5–20 atmospheres (H. O. House, Modern Synthetic Reactions, Chapter 1, N. A. Benjamin Inc., Menlo Park, Calif. 1972).

In accordance with the process of this invention, a compound of formula I is usually obtained as an isomeric mixture. In this isomer mixture, the preferred α-double bond isomer usually is the major product.

If desired, the isomer mixture can be separated into its individual components by methods known in the art, for example by preparative gas chromatography. This method is especially suitable for the preparation of the pure α-isomers. The isomers of the compounds of formula I do not have fundamentally different organoleptic properties, so that especially for economical reasons, it is preferred to use the isomer mixture.

The compounds of formula I have particular organoleptic properties which make them excellently suited as odorant substances. The invention is therefore also concerned with the use of the compounds of formula I as odorant substances.

On the basis of their natural odour notes the compounds of formula I are particularly suitable for the modification of known compositions. They have in general a woody-powdery character. The interesting precious wood note, which has good fixation, is accompanied in general by slight amber-like, spicy-peppery side notes.

The odours of compounds of formula I are as follows:

| Compound | odour |
|---|---|
| [1] 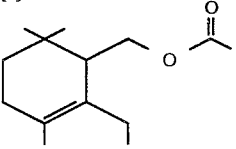 | dry, woody, spicy-peppery, amber-like. |
| [2] 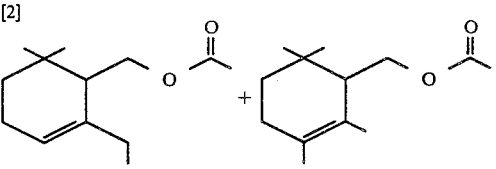 (mixture) | woody, camphorous, amber-like. |
| [3] 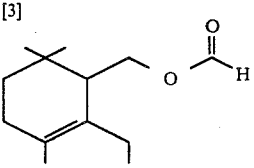 | woody, camphorous, powdery. |
| [4] 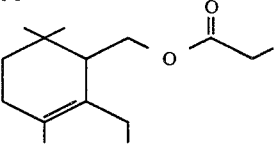 | woody, slightly sourish, fatty. |
| [5] 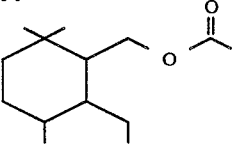 | camphorous, woody-cedar like, spicy, reminiscent of patchouli. |
| [6] 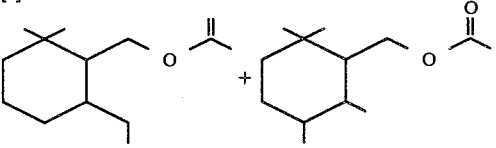 (mixture) | precious wood note powdery, distant ionone-like. |
| [7] 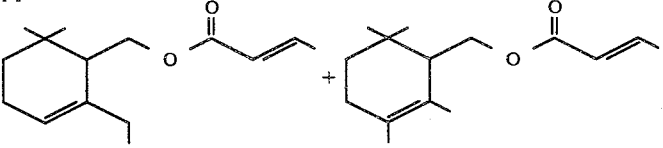 (mixture) | butter-like, powdery in the dry-out. |

| Compound | odour |
|---|---|
| [8] 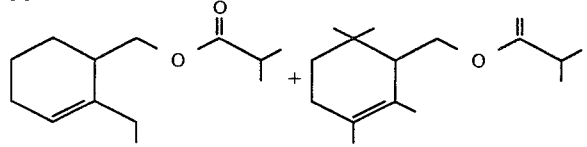 (mixture) | aldehydic, fatty, agrestic (especially of eucalyptus seeds). |

The esters of formula I are compatible with numerous known natural or synthetic ingredients of odorant substance compositions, whereby the range of the natural ingredients can embrace not only readily-volatile but also semi-volatile and non-volatile substances, and the range of the synthetic ingredients can embrace representatives from practically all classes of substances, as will be evident from the following compilation:

Natural products such as basil oil, bergamot oil, cedarwood oil, coriander oil, tree moss absolute, elemi oil, pine-needle oil, galbanum oil, jasmine absolute and its reconstituted substitute, patchouli oil, petitgrain oil Paraguay, sandalwood oil, lemon oil etc.

Alcohols such as citronellol, linalool, cis-6-nonenol, phenylethyl alcohol, rhodinol (rhodinol/citronellol mixture), α-terpineol, cinnamic alcohol or its toxicologically harmless substitutes etc.

Aldehydes such as cyclamen aldehyde, decanal, hydroxycitronellal, Lilial® (p-tert.butyl-α-methylhydrocinnamaldehyde), etc.

Ketones such as p-methyl-acetophenone, methyl ionone etc.

Esters such as ethyl acetoacetate, ortho- and para-tert.butylcyclohexyl acetate, cedryl acetate, cinnamyl formate, geranyl acetate, cis-3-hexenyl salicylate, maltyl isobutyrate, methyl dihydrojasmonate, Myraldylacetate TM ([4-(4-methyl-3-pentenyl)-3-cyclohexen-1-yl]methyl acetate), terpenyl acetate etc.

Lactones such as γ-undecalactone etc.

Nitrogen or sulphur-containing compounds such as indole, p-methane-8-thiol-3-one etc.

Musk compounds such as musk ketone, Mush 174 TM (12-oxahexadecanolide) etc.

Also worthy of mention is the manner in which the compounds of formula I round-off and harmonize the odour notes of known compositions without, dominating them.

The compounds of formula I, or mixtures thereof, can be used in wide limits which, for example, can extend in compositions from 0.1% in the case of detergents to 30% in the case of alcoholic solutions. It will be appreciated that these values are not limiting values, since the experienced perfumer can also achieve effects with lower concentrations or can synthesize novel complexes with higher concentrations. The preferred concentrations vary between 0.5% and 25%. The compositions produced with compounds of formula I can be used for all kinds of perfumed consumer goods (eau de cologne, eau de toilette, essences, lotions, creams, shampoos, soaps, salves, powders, toothpastes, mouth washes, deodorants, detergents etc.).

The compounds of formula I, or mixtures thereof can therefore be used in the production of compositions and, as will be evident from the foregoing compilation, using a wide range of known odorant substances or odorant substance mixtures. In the production of such compositions the known odorant substances or odorant substance mixtures specified earlier can be used according to methods known to the perfumer such as, for example, according to W. A. Poucher, Perfumes, Cosmetics, Soaps 2, 7th Edition, Chapman and Hall, London 1974.

The alcohols of formula II which are used as starting materials for the manufacture of the compounds of formula I are novel and also form an object of the present invention. These alcohols are also odorant substances, but they are altogether weaker and have more camphorous notes than the compounds of formula I. The compounds of formula I are therefore preferred over the alcohols of formula II.

The alcohols of formula II can be prepared as follows:

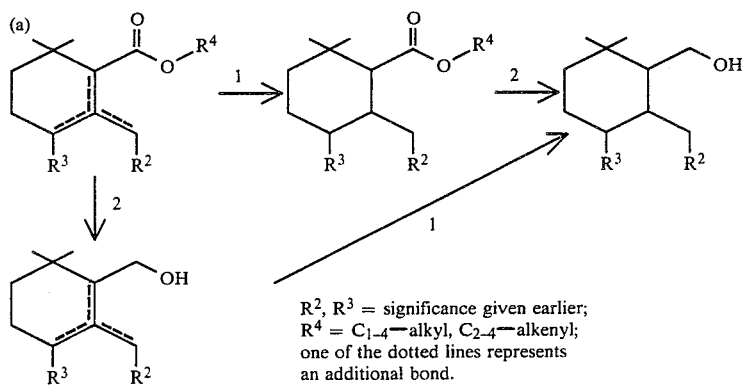

$R^2$, $R^3$ = significance given earlier;
$R^4$ = $C_{1-4}$—alkyl, $C_{2-4}$—alkenyl;
one of the dotted lines represents
an additional bond.

1 Catalytic hydrogenation; under the conditions given earlier.
2 Reduction:
(a) According to Bouveault-Blanc; see, for example, H.O. House, Modern Synthetic Reactions, 2nd Edition, Chapter 3, W. A. Benjamin Inc., Menlo Park, Cal. 1972.
(b) With metal hydrides; see, for example, H.O. House, Modern Synthetic Reactions, 2nd Edition, Chapter 2, W. A. Benjamin Inc., Menlo Park, Cal. 1972.

The following Examples illustrate the present invention:

EXAMPLE 1

25 g (0.137 mol) of an alcohol mixture consisting of about 80% of 2-ethyl-3,6,6-trimethyl-2-cyclohexene-1-methanol (remainder: double bond isomers), 15.4 g of acetic anhydride and 13 g of pyridine are stirred at 60° C. for 15 hours. The mixture is diluted with hexane and subsequently washed neutral with 2N hydrochloric acid, 2N sodium carbonate solution and finally with brine, dried over sodium sulphate and freed from solvent on a rotary evaporator. The crude product (30.3 g) is fractionally distilled over a 5 cm Widmer column in a high vacuum. There are obtained 24.4 g (79.3% of theory) of an ester mixture of boiling point 63°–64° C./0.09 mm Hg consisting of about 80% of 2-ethyl-3,6,6-trimethyl-2-cyclohexene-1-methyl acetate (remainder: double bond isomers); $n_D^{20}$ = 1.4675.

| IR (liq.): | 1745 cm$^{-1}$ | (C=O, ester) | |
|---|---|---|---|
| NMR (CDCl$_3$): | 0.87 | } each s (3H) | C$_6$ $\diagup$ CH$_3$ $\diagdown$ CH$_3$ |
| | 0.94 | | |
| | 0.93 | t/7(3H) | C$_2$—CH$_2$—CH$_3$ |
| | 1.60 | s(3H) | C$_3$—CH$_3$ |
| | 2.00 | s(3H) | O ‖ C—CH$_3$ |
| MS: | 4.01 | d/5(2H) | C$_1$—CH$_2$—O— |
| | 224(M, 1), 43(100), 164(79), 149(78), 93(56), 12(43) | | |

The alcohol mixture used as the starting material is prepared as follows: 9.7 g (0.256 mol) of lithium aluminium hydride are placed in 600 ml of absolute diethyl ether. The suspension is cooled to 10° C. At this temperature there is added dropwise within 2 hours a solution of 100 g of an ester mixture containing about 80% of ethyl 2-ethyl-3,6,6-trimethyl-2-cyclohexene-1-carboxylate (remainder: double bond isomers) in 150 ml of absolute diethyl ether. After the dropwise addition, the mixture is left to react-out at room temperature for 12 hours. The mixture is cooled to 0° C. and cautiously treated dropwise with 100 ml of an ice-cold saturated ammonium chloride solution so that the temperature does not rise above 10° C. The organic phase is separated in a separating funnel and the aqueous phase is extracted a further twice with ether. The combined organic phases are washed neutral, dried over sodium sulphate and evaporated on a rotary evaporator. The crude product (79.6 g) is fractionally distilled over a 10 cm Widmer column in a high vacuum. There are obtained 69.8 g (85.9% of theory) of an alcohol mixture of boiling point 68°–70° C./0.06 mm Hg consisting of about 80% of 2-ethyl-3,6,6-trimethyl-2-cyclohexene-1-methanol (remainder: double bond isomers); $n_D^{20}$ = 1.4839.

| IR (liq): | 3600–3100 cm$^{-1}$ | (OH) | |
|---|---|---|---|
| NMR (CDCl$_3$): | 0.88 | } each s(3H) | C$_6$ $\diagup$ CH$_3$ $\diagdown$ CH$_3$ |
| | 1.07 | | |
| | 0.98 | t/7(3H) | CH$_2$—CH$_3$ |
| | 1.70 | s(3H) | C$_3$—CH$_3$ |
| | 3.70 | d/5(2H) | C$_1$—CH$_2$—OH |
| MS: | 182(N, 10), 141(100), 95(43), 109(38), 41(27), 55(18). | | |

EXAMPLE 2

In a manner analogous to that described in Example 1, from 16.8 g (0.1 mol) of an alcohol mixture containing about 20% of 2,3,6,6-tetramethyl-2-cyclohexene-1-methanol (including double bond isomers: the isomer mixture contains more than 75% of the 2-cyclohexene derivative) and 80% of 2-ethyl-6,6-dimethyl-2-cyclohexene-1-methanol (including double bond isomers; the isomer mixture contains more than 75% of the 2-cyclohexene derivative) there are obtained 13.9 g (66.2% of theory) of an ester mixture consisting of about 20% of 2,3,6,6-tetramethyl-2-cyclohexene-1-methyl acetate (including double bond isomers; the isomer mixture contains more than 75% of the 2-cyclohexene derivative) and 80% of 2-ethyl-6,6-dimethyl-2-cyclohexene-1-methyl acetate (including double bond isomers; the isomer mixture contains more than 75% of the 2-cyclohexene derivative). Boiling point 59°–60° C./0.09 mm Hg; $n_D^{20} = 1.4661$.

The alcohol mixture used as the starting material is obtained in a yield of 91.6% of theory in a manner analogous to that described in Example 1 from an ester mixture consisting of about 20% of ethyl 2,3,6,6-tetramethyl-2-cyclohexene-1-carboxylate (including double bond isomers; the isomer mixture contains more than 75% of the 2-cyclohexene derivative) and 80% of ethyl 2-ethyl-6,6-dimethyl-2-cyclohexene-1-carboxylate (including double bond isomers; the isomer mixture contains more than 75% of the 2-cyclohexene derivative) by reduction with lithium aluminium hydride. Boiling point 48°–50° C./0.04 mm Hg; $n_D^{20} = 1.4855$.

EXAMPLE 3

10.5 g (0.228 mol) of formic acid are added dropwise to 18.6 g (0.182 mol) of acetic anhydride. The mixture is warmed to 50° C. for 15 minutes and subsequently cooled to 0° C. At this temperature there are added dropwise 25 g (0.137 mol) of an alcohol mixture containing about 80% of 2-ethyl-3,6,6-trimethyl-2-cyclohexene-1-methanol (remainder: double bond isomers). The mixture is left to react-out at a temperature of 0°–5° C. for 12 hours. The mixture is taken up in 50 ml of hexane, washed neutral with water, with 2N sodium carbonate solution and again with water, dried over sodium sulphate and concentrated on a rotary evaporator. The crude product (27.5 g) is fractionally distilled over a 10 cm Widmer column in a high vacuum. There are obtained 21.8 g (75.6% of theory) of an ester mixture containing about 80% of 2-ethyl-3,6,6-trimethyl-2-cyclohexene-1-methyl formate (remainder: double bond isomers). Boiling point 52°–54° C./0.04 mm Hg; $n_D^{20} = 1.4721$.

| IR (liq.): | 1730 cm$^{-1}$ | | |
|---|---|---|---|
| NMR (CDCl$_3$): | 0.90<br>0.99 | } each s(3H) | $C_6\begin{array}{c}CH_3\\ \diagdown \\ CH_3\end{array}$ |
| | 0.95 | t/7(3H) | $C_2$—$CH_2$—$\underline{CH}_3$ |
| | 1.66 | s(3H) | $C_3$—$\underline{CH}_3$ |
| | 4.15 | d/5(2H) | $C_1$—$\underline{CH}_2$—O— |
| | 8.02 | s(1H) | $\begin{array}{c}O\\ \parallel\\ -OC-\underline{H}\end{array}$ |
| MS: | 151(100), 41(98), 93(96), 164(93), 95(88), 149(86). | | |

The alcohol mixture used as the starting material is obtained according to the procedure described in Example 1.

EXAMPLE 4

25 g (0.137 mol) of an alcohol mixture which consists of about 80% of 2-ethyl-3,6,6-trimethyl-2-cyclohexene-1-methanol (remainder: double bond isomers), 19.6 g (0.151 mol) of propionic anhydride and 13.0 g of pyridine are stirred at 60° C. for 12 hours. The mixture is diluted with hexane and subsequently washed neutral with 2N hydrochloric acid, 2N sodium carbonate solution and brine, dried over sodium sulphate and evaporated on a rotary evaporator. The crude product (30.4 g) is fractionally distilled over a 10 cm Widmer column in a high vacuum. There are obtained 26.2 g (80.1% of theory) of an ester mixture consisting of about 80% of 2-ethyl-3,6,6-trimethyl-2-cyclohexene-1-methyl propionate (remainder: double bond isomers). Boiling point 75°–76° C./0.05 mm Hg; $n_D^{20} = 1.4672$.

| IR (liq.): | 1740 cm$^{-1}$ | | |
|---|---|---|---|
| NMR (CDCl$_3$): | 0.87<br>0.97 | } each s(3H) | $C_6\begin{array}{c}CH_3\\ \diagdown \\ CH_3\end{array}$ |
| | 0.92 | t/7(3H) | $C_2$—$CH_2$—$\underline{CH}_3$ |
| | 1.59 | s(3H) | $C_3$—$\underline{CH}_3$ |
| | 4.03 | d/s(2) | $C_2$—$\underline{CH}_2$—O— |
| MS: | 164(100), 149(99), 29(84), 57(81), 135(55), 151(51). | | |

The alcohol mixture used as the starting material is obtained according to the procedure described in Example 1.

EXAMPLE 5

A mixture of 10 g (54.3 mmol) of 2-ethyl-3,6,6-trimethyl-cyclohexane-1-methanol (4 stereoisomers), 15 ml of acetic anhydride and 100 ml of pyridine is left to stand at room temperature for 12 hours. Excess pyridine and acetic anhydride are distilled off on a rotary evaporator at a bath temperature of about 50° C. in a water-jet vacuum. The residue is taken up in hexane, washed neutral with 2N hydrochloric acid, saturated sodium bicarbonate solution and water, dried over sodium sulphate and evaporated. The crude product (11.4 g) is fractionally distilled over a 10 cm Vigreux column in a high vacuum. There are thus obtained 7.0 g (57.0% of theory) of 2-ethyl-3,6,6-trimethyl-cyclohexane-1-methyl acetate (4 stereoisomers) of boiling point 65°–67° C./0.08 mm Hg; $n_D^{20} = 1.4599$.

IR (liq.): 1740 cm$^{-1}$ (C=O, ester)

MS: 43(100), 55(75), 59(58), 81(50), 95(49), 41(48).

The 2-ethyl-3,6,6-trimethyl-cyclohexane-1-methanol (4 stereoisomers) used as the starting material is obtained in 97.5% yield in a manner analogous to that described in Example 1 from ethyl 2-ethyl-3,6,6-trimethyl-cyclohexane-1-carboxylate (4 stereoisomers) by reduction with lithium aluminium hydride. Boiling point 75°/0.05 mm Hg; $n_D^{20} = 1.4763$.

The ethyl 2-ethyl-3,6,6-trimethyl-cyclohexane-1-carboxylate is prepared as follows:

22.4 g (0.1 mol) of an ester mixture consisting of about 80% of ethyl 2-ethyl-3,6,6-trimethyl-2-cyclohexene-1-carboxylate (remainder: double bond isomers) are dissolved in 250 ml of absolute ethanol and hydrogenated with the addition of 800 mg of palladium (10%) on carbon) in an autoclave at 10 bar and 60° C. for 24 hours. The catalyst is filtered off over Celite, rinsed with a small amount of ethanol and the solvent is distilled off on a rotary evaporator.

The crude product (21.8 g) is fractionally distilled over a 5 cm Widmer column in a high vacuum. There are obtained 18.0 g (79.6% of theory) of a mixture of boiling point 80°–81°/0.15 mm Hg; $n_D^{20} = 1.4527$. In a capillary gas chromatogram (50 m × 0.31 mm i.d., Ucon HB 5100, 140° C. isothermal, helium flow 2.5 ml/minute split ratio 1:30) there are visible 4 peaks with the following percentage amounts of the total mixture (listed according to increasing retention time):

| | |
|---|---|
| P₁ | 42.4% |
| P₂ | 34.9% |
| P₃ | 16.5% |
| P₄ | 6.2% |

Peaks 1, 2, 3 and 4 represent the 4 possible stereoisomers of ethyl 2-ethyl-3,6,6-trimethyl-cyclohexane-1-carboxylate.

EXAMPLE 6

A mixture of 10 g (58.8 mmol) of about 80% of 2-ethyl-6,6-dimethyl-cyclohexane-1-methanol (2 stereoisomers) and about 20% of 2,3,6,6-tetramethyl-cyclohexane-1-methanol (4 stereoisomers) is left to stand at room temperature for 12 hours together with 15 ml of acetic anhydride and 100 ml of pyridine. Excess pyridine and acetic anhydride are distilled off on a rotary evaporator at a bath temperature of about 50° C. in a water-jet vacuum. The residue is taken up in hexane, washed neutral with 2N hydrochloric acid, saturated sodium bicarbonate solution and water, dried over sodium sulphate and evaporated. The crude product (10.9 g) is fractionally distilled over a 5 cm Vigreux column in a high vacuum. There are thus obtained 6.8 g (54.5% of theory) of a mixture consisting of about 80% of 2-ethyl-6,6-dimethyl-cyclohexane-1-methyl acetate (2 stereoisomers) and 20% of 2,3,6,6-tetramethyl-cyclohexane-1-methyl acetate (4 stereoisomers) of boiling point 67°–68° C./0.06 mm Hg; $n_D^{20}=1.4571$.

The mixture used as the starting material is obtained in a yield of 71.2% of theory in a manner analogous to that described in Example 1 from a mixture consisting of about 80% of ethyl 2-ethyl-6,6-dimethyl-cyclohexane-1-carboxylate and 20% of ethyl 2,3,6,6-tetramethyl-cyclohexane-1-carboxylate by reduction with lithium aluminium hydride. Boiling point 72° C./0.05 mm Hg; $n_D^{20}=1.4746$.

The foregoing ethyl ester mixture is prepared as follows:

To a cooled solution of 5.8 g (0.252 g atom) of sodium in 130 ml of absolute ethanol is added dropwise at a temperature of 5°–10° C. a solution of 30 g (0.214 mol) of a ketone mixture (consisting of 20% of 3,6-dimethyl-5-hepten-2-one and 80% of 7-methyl-6-octen-3-one) and 62.4 g (0.278 mol) of triethyl phosphonoacetate in 130 ml of absolute toluene. Subsequently, the mixture is left to come to room temperature and to react-out for 12 hours. The mixture is poured into ice-water and extracted 3 times with hexane. The combined hexane solutions are washed neutral with sodium chloride solution, dried over sodium sulphate and evaporated. The crude product (43 g) is fractionally distilled in a high vacuum over a 10 cm Widmer column. There are obtained 28.9 g (64.3%) of a mixture of boiling point 58°–61° C./0.02 mm Hg; $n_D^{20}=1.4708$. The mixture consists of 20% of ethyl c,t-3,4,7-trimethyl-2,6-octadienoate and 80% of ethyl c,t-3-ethyl-7-methyl-2,6-octadienoate.

228 ml of formic acid are cooled to 0°–5° C. At this temperature there are added 12 ml of concentrated sulphuric acid and subsequently the mixture is stirred for 1 hour. To the resulting acid mixture there are cautiously added dropwise at +5° C. 24 g of the foregoing ester mixture consisting of 20% of ethyl c,t-3,4,7-trimethyl-2,6-octadienoate and 80% of ethyl c,t-3-ethyl-7-methyl-2,6-octadienoate. After completion of the addition, the mixture is left to come to room temperature and it is stirred at this temperature for a further 1 hour. The mixture is poured on to ice and extracted 3 times with hexane. The combined hexane solutions are washed neutral with water (once), with sodium bicarbonate solution (twice) and finally with water (twice), dried over sodium sulphate and evaporated. The crude product (22.5 g) is fractionally distilled in a high vacuum on a 10 cm Widmer column. There are obtained 17 g (70.8%) of an ester mixture consisting of about 20% of ethyl 2,3,6,6-tetramethyl-2-cyclohexene-1-carboxylate, 14% of ethyl c,t-2-ethylidene-6,6-dimethylcyclohexane-1-carboxylate and 65% of ethyl 2-ethyl-6,6-dimethyl-2-cyclohexene-1-carboxylate of boiling point 102° C./6 mm Hg; $n_D^{20}=1.4626$.

30 g of the foregoing ester mixture are dissolved in 300 ml of absolute ethanol and hydrogenated with the addition of 600 mg of palladium (10% on carbon) while stirring well at normal pressure. 96.9% of the theoretical amount of hydrogen are taken up after 24 hours. The catalyst is filtered off over Celite, rinsed with a small amount of ethanol and the solvent is distilled off on a rotary evaporator.

The crude product (29.8 g) is fractionally distilled over a 10 cm Widmer column in a high vacuum. There are obtained 28 g (92.4% of theory) of a mixture of boiling point 42°–55° C./0.05 mm Hg. In accordance with gas chromatography [glass capilliary column (50 m×0.3 mm i.d.) with Ucon HB 5100 as the stationary phase, 140° isothermal, helium flow 2.5 ml/minute] the product has essentially the following composition: 43.6% of ethyl cis-2-ethyl-6,6-dimethylcyclohexane-1-carboxylate, 36.4% of ethyl trans-2-ethyl-6,6-dimethyl-cyclohexane-1-carboxylate and 20.0% of ethyl 2,3,6,6-tetramethylcyclohexane-1-carboxylate (various stereoisomers, inter alia about 4.1% of ethyl 1,2-cis-2,3-trans-2,3,6,6-tetramethyl-1-cyclohexanecarboxylate and about 9.1% of ethyl 1,2 trans-2,3,6,6-tetramethyl-1-cyclohexanecarboxylate). The isomer mixture was separated by means of preparative gas chromatography. The main peaks showed the following spectroscopic data:

| IR (liq.) 1735 cm⁻¹ | ¹H—NMR (360 MHz, CDCl₃): |
|---|---|
| Ethyl cis-2-ethyl-6,6-dimethyl-cyclohexane-1-carboxylate | |

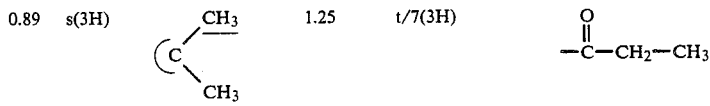

-continued

| IR (liq.) 1735 cm$^{-1}$ | | | $^1$H—NMR (360 MHz, CDCl$_3$): | | |
|---|---|---|---|---|---|
| 0.91 | t/7(3H) | —CH$_2$—CH$_3$ | 2.31 | d/4(1H) | ⟩C⟨H / C(=O)—CH$_2$—CH$_3$ |
| 0.99 | s(3H) | ⟩C⟨CH$_3$/CH$_3$ | 4.09 | AB part of ABX$_3$ (2H) | O=C—O—C(H$_a$)(H$_b$)—CH$_3$ |

Ethyl trans-2-ethyl-6,6-dimethyl-cyclohexane-1-carboxylate

| 0.86 | t/7(3H) | —CH$_2$—CH$_3$ | 1.26 | t/7(3H) | —C(=O)—CH$_2$—CH$_3$ |
| 0.93 | s(3H) | ⟩C⟨CH$_3$/CH$_3$ | 1.89 | d/11.5(1H) | ⟩C⟨H / C(=O)—CH$_2$—CH$_3$ |
| 0.97 | s(3H) | ⟩C⟨CH$_3$/CH$_3$ | 4.13 | q/7(2H) | C(=O)—CH$_2$—CH$_3$ |

Ethyl 1,2-cis, 2,3-trans, 2,3,6,6-tetramethyl-1-cyclohexanecarboxylate

| 0.86 | d/7(3H) | C$_3$—CH$_3$ | 1.40–1.60 | m(2H) | i.a. C$_2$—H$_{ax}$ |
| 0.87 | d/t(3H) | C$_2$—CH$_3$ | 1.68–1.81 | m(1H) | C$_3$—H$_{ax}$ |
| 0.89 | s(3H) | C$_6$⟨CH$_3$/CH$_3$ | 1.84–1.95 | m(1H) | C$_5$—H$_{ax}$ |
| 0.99 | s(3H) | | | | |
| 1.25 | t/7(3H) | O=C—CH$_2$—CH$_3$ | 4.10 | q/7(2H) | O=C—CH$_2$—CH$_3$ |

Ethyl 1,2-trans, 2,3-trans-2,3,6,6-tetramethyl-1-cyclohexanecarboxylate

| 0.84 | d/6(3H) | C$_3$—CH$_3$ | 1.26 | t/7(3H) | O=C—CH$_2$—CH$_3$ |
| 0.925 | s(3H) | C$_6$—CH$_3$ | 1.87 | d/7(1H) | C$_1$—H$_{ax}$ |
| 0.93 | d/6(3H) | C$_2$—CH$_3$ | 4.14 | q/7(2H) | O=C—CH$_2$—CH$_3$ |
| 0.95 | s(3H) | C$_6$—CH$_3$ | | | |

EXAMPLE 7

In a manner analogous to that described in Example 1 (but using crotonic anhydride) there are obtained from 14.0 g (0.083 mol) of an alcohol mixture consisting of about 20% of 2,3,6,6-tetramethyl-2-cyclohexene-1-methanol (including double bond isomers; the isomer mixture contains more than 75% of the 2-cyclohexene compound) and 80% of 2-ethyl-6,6-dimethyl-2-cyclohexene-1-methanol (including double bond isomers; the isomer mixture contains more than 75% of the 2-cyclohexene compound) 15.4 g (78.3% of theory) of an ester mixture consisting of about 20% of 2,3,6,6-tetramethyl-2-cyclohexene-1-methyl crotonate (including double bond isomers; the isomer mixture contains more than 75% of the 2-cyclohexene compound) and 80% of 2-ethyl-6,6-dimethyl-2-cyclohexane-1-methyl crotonate (including double bond isomers; the isomer mixture contains more than 75% of the 2-cyclohexene compound). Boiling point 83°–85° C./0.06 mm Hg; n$_D^{20}$=1.4826.

The alcohol mixture used as the starting material is obtained in a yield of 91.6% of theory in a manner analogous to that described in Example 1 from an ester mixture consisting of about 20% of ethyl 2,3,6,6-tetramethyl-2-cyclohexene-1-carboxylate (including double bond isomers; the isomer mixture contains more than 75% of the 2-cyclohexene compound) and 80% of ethyl 2-ethyl-6,6-dimethyl-2-cyclohexene-1-carboxylate (including double bond isomers; the isomer mixture contains more than 75% of the 2-cyclohexene compound) by reduction with lithium aluminium hydride. Boiling point 48°–50° C./0.04 mm Hg; $n_D^{20} = 1.4855$.

EXAMPLE 8

Perfumery base in the direction of chypre

|  | Parts by weight |
| --- | --- |
| Methyl 1-methylcyclododecyl ether | 200 |
| Bergamot oil | 150 |
| Hydroxycitronellal | 100 |
| Pine oil Pumillon | 80 |
| Citronellol | 80 |
| Petitgrain oil | 60 |
| Musk 174 TM Giv (12-oxahexadecanolide) | 60 |
| Coriander oil | 40 |
| Galbanum oil | 40 |
| Patchouli oil | 40 |
| Lemon oil | 40 |
| Elemi oil | 10 |
| Tree moss decolourized | 20 |
|  | 920 |

The addition of 40 parts of the ester mixture of Example 1 has a very harmonizing effect on the odour properties of the foregoing base. The somewhat herby note of the elemi-cedarwood complex in the original base is advantageously combined with the flowery mixture hydroxycitronellol-citronellol, so that this dominates in the resulting composition.

If 40 parts of the ester of Example 5 are added to the foregoing chypre base, then the base gains in fullness and warmth. The fresh impression which also occurs and which makes the novel base suitable for the perfuming of soaps and deodorants is surprising.

EXAMPLE 9

Perfumery base in the direction of melon

|  | Parts by weight |
| --- | --- |
| Myraldylacetat TM Giv [[4-(4-methyl-3-pentenyl)-3-cyclohexen-1-yl]methyl acetate] | 140 |
| Hexenyl salicylate | 80 |
| Methyl dihydrojasmonate | 60 |
| Ethyl acetoacetate | 60 |
| Cyclamen aldehyde | 50 |
| ortho-Tert.butyl-cyclohexyl acetate | 50 |
| Lilial ® Giv (p-tert.butyl-α-methylhydrocinnamaldehyde) | 10 |
| Rhodinol | 5 |
| Eugenol | 5 |
| Maltyl isobutyrate (10% in DPG) | 5 |
| Acetanisole | 5 |
| cis-6-Nonenol (10% in DPG) | 5 |
| Dipropylene glycol (DPG) | 425 |
|  | 900 |

By adding 100 parts of the ester mixture of Example 1 the original green-fatty melon character is modified in the direction of a succulent-fruity, fresh melon character. The novel base has a pronounced naturalness. This fresh melon character is the goal which is striven for in this composition.

EXAMPLE 10

Woody base

|  | Parts by weight |
| --- | --- |
| Bergamot oil | 200 |
| Patchouli oil | 200 |
| Sandalwood oil | 200 |
| Cedryl acetate | 100 |
| Methyl dihydrojasmonate | 70 |
| Methyl ionone | 50 |
| p-Tert.butylcyclohexyl-2 acetate | 50 |
| Basil oil | 30 |
|  | 900 |

The addition of 100 parts of the ester mixture of Example 1 brings about an extremely surprising effect. The evaluation in the freshly dipped condition shows that a fresh, rustic-herby cologne note suddenly predominates in the woody composition. Likewise, the bottom note of the novel composition behaves unexpectedly; the novel substance confers to the bottom a pronounced vetiver note, although vetiver oil is not an ingredient of this composition.

EXAMPLE 11

General flowery perfumery base

|  | Parts by weight |
| --- | --- |
| Terpineol | 260 |
| Hydroxycitronellal | 220 |
| Cinnamic alcohol substitute | 120 |
| Phenylethyl alcohol | 100 |
| Cinnamyl formate | 20 |
| Linalool | 15 |
| Terpenyl acetate | 10 |
| Musk ketone | 10 |
| Geranyl acetate | 10 |
| Jasmine synthetic | 10 |
| Eugenol | 5 |
| Indole (10% in DPG) | 5 |
| C—10-aldehyde (10% in DPG) | 5 |
| p-Methylacetophenone | 5 |
| Undecalactone | 5 |
|  | 800 |

The addition of 200 parts of the ester mixture of Example 6 confers a pronounced hyacinth note to this generally flowery base in the direction of lilac. This is all the more remarkable, since the novel ester mixture has no flowery notes.

I claim:

1. A method for improving the odor of a fragrance composition which comprises adding thereto an olfactorily effective amount of a mixture of 2-ethyl-6,6-dimethyl-2-cyclohexene-1-methyl acetate and 2,3,6,6-tetramethyl-2-cyclohexene-1-methyl acetate.

2. A method according to claim 1 wherein the ratio of 2-ethyl-6,6-dimethyl-2-cyclohexene-1-methyl acetate to 2,3,6,6-tetramethyl-2-cyclohexene-1-methyl acetate is about four to one.

3. A method for improving the odor of a fragrance composition which comprises adding thereto an olfactorily effective amount of 2-ethyl-3,6,6-trimethyl-2-cyclohexene-1-methyl acetate.

4. A fragrance composition comprising an olfactorily effective amount of a mixture of 2-ethyl-6,6-dimethyl-2-cyclohexene-1-methyl acetate and 2,3,6,6-tetramethyl-2-cyclohexene-1-methyl acetate and at least one other olfactory substance.

5. A fragrance composition according to claim 4 wherein the ratio of 2-ethyl-6,6-dimethyl-2-cyclohexene-1-methyl acetate to 2,3,6,6-tetramethyl-2-cyclohexene-1-methyl acetate is about four to one.

6. A fragrance composition comprising an olfactorily effective amount of 2-ethyl-3,6,6-trimethyl-2-cyclohexene-1-methyl acetate and at least one other olfactory substance.

7. The mixture 2-ethyl-6,6-dimethyl-2-cyclohexene-1-methyl acetate and 2,3,6,6-tetramethyl-2-cyclohexene-1-methyl acetate.

8. A compound according to claim 7 wherein the ratio of 2-ethyl-6,6-dimethyl-2-cyclohexene-1-methyl acetate to 2,3,6,6-tetramethyl-2-cyclohexene-1-methyl acetate is about four to one.

9. The compound 2-ethyl-3,6,6-trimethyl-2-cyclohexene-1-methyl acetate.

* * * * *